United States Patent [19]

Ehrlich et al.

[11] Patent Number: 5,510,341

[45] Date of Patent: * Apr. 23, 1996

[54] OVULATION-INHIBITING PREPARATION FOR HORMONAL CONTRACEPTION

[75] Inventors: Marika Ehrlich, Bahnhofstrasse 1, 6509 Framersheim; Herbert Kuhl, Hotzelstrasse 18, 8750 Aschaffenburg, both of Germany

[73] Assignees: Marika Ehrlich, Fremersheim; Herbert Kuhl, Aschaffenburg, both of Germany

[ * ] Notice: The portion of the term of this patent subsequent to Jan. 18, 2011, has been disclaimed.

[21] Appl. No.: 132,287

[22] Filed: Oct. 6, 1993

Related U.S. Application Data

[63] Continuation of Ser. No. 833,294, Feb. 10, 1992, Pat. No. 5,280,023.

[30] Foreign Application Priority Data

Feb. 9, 1991 [DE] Germany ............... 41 04 385.5

[51] Int. Cl.⁶ .................................................. A61K 31/56
[52] U.S. Cl. ........................ 514/177; 514/170; 514/178; 514/182; 514/843
[58] Field of Search ................................ 514/170, 177, 514/178, 182, 843

[56] References Cited

U.S. PATENT DOCUMENTS 3,733,407  5/1973  Segre ........................ 424/239
4,921,843  5/1990  Pasquale ..................... 514/170

FOREIGN PATENT DOCUMENTS 0036229  9/1981  European Pat. Off. .
0368373  5/1990  European Pat. Off. .

OTHER PUBLICATIONS

Paul E. Lebech, *Virker Menonorm tilstraekkelig antikonceptionelt hos praeklimakterielle kvinder?*, Ugeskritt for Laeger, vol. 141/8, 1979, pp. 523–524.

Frode Gam et al., *Hormonbehandling af Klimakterielle gener*, Ugeskrift for Laeger, 1977, vol. 139/47, pp. 2808–2812.

Primary Examiner—Kimberly R. Jordan
Attorney, Agent, or Firm—Hill, Steadman & Simpson

[57] ABSTRACT

An ovulation-inhibiting preparation for hormonal contraception, comprising two hormone constituents packed spatially separate in a packing unit intended for chronological, sequential oral administration, said constituents each comprising a plurality of daily hormone units accommodated spatially separate and individually removable in the packaging unit. The first hormone constituent consists essentially of an estrogen preparation which effects a disturbance of the follicle stimulation; the second hormone constituent consists of an estrogen preparation and a gestagen preparation in a dose at least adequate for inhibiting ovulation. The total number of daily hormone units is equal to the total number of days in the desired cycle, and the number of daily units of the first hormone constituent is less than the number of daily units of the second hormone constituent. The first hormone constituent comprises 5 to 14 daily units, and the second hormone constituent comprises 23 to 14 daily units.

8 Claims, No Drawings

OVULATION-INHIBITING PREPARATION FOR HORMONAL CONTRACEPTION

This is a continuation of application Ser. No. 07/833,294 filed Feb. 10, 1992, now U.S. Pat. No. 5,280,023.

BACKGROUND OF THE INVENTION

The present invention relates to a preparation for hormonal contraception. More specifically, the present invention relates to an ovulation-inhibiting preparation for hormonal contraception.

Hormonal ovulation inhibitors, which are orally administered in daily units, include combination preparations and sequential preparations. In combination preparations, a combination of an estrogen preparation and a gestagen preparation is administered for 21 days in constant or alternating, or absolute and/or relative dosing, to the extent that the desired cycle duration is 28 days. The estrogen preparation can be a natural estrogen or a synthetic ethinyl estradiol. After the administration of the aforementioned 21 daily units, this dosing is followed by a 7-day pause, whereby withdrawal bleeding simulating the natural menses occurs.

With typical sequential preparations that are given during a desired cycle duration of 28 days, a pure estrogen preparation is administered for 7 days and then a combination of an estrogen preparation and a gestagen preparation is administered for 15 days. An administration-free time of, for example, six days follows, during which withdrawal bleeding occurs. Although it is known to bridge the administration pause time in the combination and the sequential preparations with placebos for the sake of greater reliability of administration, no hormones of the type previously discussed have been administered during the approximately one-week administration pause to guarantee reliable withdrawal bleeding.

Only in substitution preparations have hormones been administered over the entire cycle. For example, a preparation has been administered in the following sequence: 10 days of an estrogen preparation, 11 days of a combination of estrogen and gestagen preparation, and 7 days of estrogen preparation in an especially low dose. These substitution preparations, however, are not suitable for inhibiting ovulation.

The sequential preparations used in substitution therapy are unsuitable for contraception, particularly because the natural estradiol does not prevent ovulation in the given dose and the phase during which gestagen is administered (i.e., 11 days) is too short. The sequential arrangement set forth above, however, does guarantee relatively good cycle control in the case of the substitution of preparations.

In general, the three most important aspects that are considered in hormonal contraception are contraceptive reliability, cycle control as well as minimum side-effects. The contraceptive reliability is based mainly on the action of the gestagen constituent. In a given preparation, gestagen is utilized in a dose that is approximately twice as high as the dose necessary for inhibiting ovulation. Added thereto are the peripheral effects of the gestagen on the cervix, fallopian tubes, and endometrium. Consequently, gestagen is present in an adequate dose in modern oral contraceptives in order to guarantee reliable contraception. The synthetic estrogen normally used, ethinyl estradiol, additionally intensifies the ovulation-inhibiting effect of the gestagen. Combined ethinyl estradiol-gestagen preparations that are taken over three weeks of four weeks with an administration pause of 7 days have, hitherto, shown the greatest contraceptive reliability.

In contrast, the sequential preparations are somewhat less reliable in view of their contraceptive reliability, since 50 µg ethinyl estradiol are administered during the pure estrogen phase which lasts about 7 days. This preparation does not prevent ovulation in all women, and also lacks the peripheral contraceptive effects of the gestagen. The ovulation-inhibiting dose (100% of women) of ethinyl estradiol is 100 µg daily.

While the combination preparations described hereinabove offer the greatest contraceptive reliability among known ovulation inhibitors, the best cycle control (i.e., regular withdrawal menses with optimally few intermenses) is achieved with the use of sequential preparations, including those of the type that effect proliferation of the endometrium. This is due to the 7-day action of the estrogen (unimpeded by gestagen) prior to the gestagen being added. Beginning with the eighth day, further proliferation is inhibited and the endometrium is thereby altered. As previously noted, a menstruation-like withdrawal bleeding occurs approximately 2 to 3 days after the last estrogen-gestagen tablet is administered. In contrast, the proliferation of the endometrium is reduced from the very outset with the use of combination preparations, so that the cycle control in the latter case is poorer than with use of the sequential preparations.

With the use of ethinyl estradiol as the estrogen constituent in sequential preparations, it has been shown that higher doses are necessary, particularly during the initial phase in order to guarantee contraceptive effectiveness. However, this, in turn, creates a risk of serious and dangerous complications or side-effects (i.e., thromboembolism). The gestagen thus employed can intensify this effect in some cases. Further, this risk increases with increasing age, and is especially pronounced in women over 40 years of age.

One solution to the aforementioned problem would be the use of combination preparations which contain the natural estrogen, estradiol, instead of ethinyl estradiol. Based on substitution therapies involving post-menopausal women, it is known that treatment with estradiol involves substantially fewer health risks. However, estradiol is hardly suitable for use in combination preparations. Although the gestagen constituent in the combination preparation thereby guarantees reliable contraception, gestagen causes an intensified inactivation of the estradiol in the endometrium. This is due to the stimulation of local enzymes. The result is that the estrogen effect on the endometrium is greatly reduced, and intermenses frequently occur involving the disadvantageous effects set forth hereinabove. By contrast, ethinyl estradiol is metabolized far more slowly in the endometrium and, consequently, has an adequate effect on the endometrium.

U.S. Patent No. 4,921,843 discloses an ovulation-inhibiting preparation of the type, wherein an administration pause of at least one day is bridged with a placebo. The placebo is provided between the administration of the last daily hormone units (i.e., dragees, tablets, or the like) of the second hormone constituent and before the new daily hormone unit (i.e., the first of the first hormone constituent of the following cycle) is administered. This is in agreement with the previously prevailing opinion in this field, namely, an administration pause of at least one day. In the alternative, a drastic reduction in the effective estrogen level was considered absolutely necessary in order to trigger withdrawal bleeding. Even when a one-day administration pause is involved, however, such a discontinuation of the estrogen leads to modifications in the body's circulation, which can cause headaches (migraine attacks) and also lead to brief-durational changes in various metabolic parameters. In particular, hemostasis can be affected, so that a stable metabolism is out of equilibrium for one or more days because of the estrogen influence.

In the preparation for treating climacteric failure phenomena disclosed by German Published Application 26 45 307, an administration pause or, at least the simulation thereof with the temporary use of an especially weak type of estrogen that does not effect any adequate disturbance of the follicle stimulation, is considered necessary. Overall, the hormone doses used, in particular the duration of the gestagen phase, are therefore inadequate for contraception in view of the preparation disclosed in the aforementioned publication.

Similarly, German Published Application 24 31 704 discloses a preparation for alleviating climacteric complaints, wherein fluctuating estrogen concentrations are provided. The gestagen doses therefore only begin after the middle of the cycle, for which reason a contraceptive effect cannot be achieved. Moreover, a hormone-free pause in administration is absolutely prescribed.

European Published Application 0 368 373 discloses an ovulation-inhibiting preparation, whereby a constant gestagen level is provided over the entire cycle duration, and estrogen phases are cyclically superimposed thereon. One disadvantage of this preparation is an increased risk of intermanses. And although the constant gestagen administration, in fact, results in a good contraceptive effect, prolonged blood vessel-constriction occurs, so that adverse health effects are likely to occur, especially in women of increasing age and those having a tendency toward circulatory problems.

SUMMARY OF THE INVENTION

The present invention provides improved ovulation-inhibiting preparations such that in addition to high contraceptive reliability, good cycle control is achieved while avoiding intermanses and side-effects.

To this end, the present invention provides an ovulation-inhibiting preparation for hormonal contraception, comprising two hormone constituents packed spatially separate in a packaging unit for chronological, sequential, oral administration. Each constituent respectively comprises a plurality of daily hormone units accommodated spatially separated and individually removable in the packaging unit. Further, the first of the hormone constituents consists essentially of an estrogen preparation which effects a disturbance of the follicle stimulation; the second hormone constituent consists of an estrogen preparation and a gestagen preparation in a dose at least adequate to inhibit ovulation in combination.

The advantages of the present invention are inventively achieved in that the total number of daily hormone units is equal to the total number of days in the desired cycle. The first hormone constituent comprises 5 to 14 daily units, while the second hormone constituent comprises 23 to 14 daily units. Further, the plurality of daily units of the first hormone constituent is less than the plurality of daily units of the second hormone constituent.

It can thereby be provided that at least one of the estrogen preparations comprises at least one constituent from the group of hormones that quickly splits off ethinyl estradiol, mestranol, other synthetic estrogens as well as at least one of the afore-mentioned hormone constituents after being ingested.

A further embodiment of the invention is characterized in that at least one of the estrogen preparations comprises at least one constituent from the group of hormones that quickly splits off estradiol, estrone and/or other natural estrogens as well as at least one of the afore-mentioned hormone constituents after ingestion.

It is also provided in the present invention that the gestagen preparation comprises at least one constituent from the group of hormones that quickly splits off progesterone, chlormadinone acetate, norethindrone acetate, cyproterone acetate, desogestrel, levonorgestrel, other natural and/or synthetic gestagens as well as at least one of the afore-mentioned hormone constituents after ingestion.

In another embodiment, the total number of daily units is 28.

In a further embodiment, the first hormone constituent comprises a maximum of 10 daily units.

In one embodiment of the invention, the first hormone constituent comprises 7 daily units and the second hormone constituent comprises 21 daily units.

In yet another embodiment of the invention, the number of daily units corresponds to the natural cycle of the woman.

Additional features and advantages of the present invention are further described, and will be apparent from the detailed description from the presently preferred embodiments.

DETAILED DESCRIPTION OF THE PRESENTLY PREFERRED EMBODIMENTS

The present invention is based, in part, on the concept that one improves contraceptive reliability as well as the cycle control by first guaranteeing hormonal control of the follicular action over the entire cycle. This is achieved by an early disturbance of the follicle stimulation within the hitherto standard hormonal administration pause, namely by the estrogen constituent to be ingested. Since an adequate build up of the mucus membrane first occurs in the pure estrogen phase, which is similar to naturally occurring conditions, intermenses occur far more rarely. This is true even with a lower dosage of the hormone constituents in the actual ovulation-inhibiting phase, wherein a combination of estrogen and gestagen is administered. The pure estrogen phase lasts at least five days and can be extended to 10 days when natural estrogen is used and up to 14 days when synthetic estrogen is used. This phase is then followed by the generally longer combined phase, depending on the duration of the desired cycle.

In a preferred embodiment of the invention, it is especially advantageous when the number of daily units of the inventive preparation corresponds to the natural, individual cycle of the woman, since an especially beneficial condition is then achieved, namely the avoidance of undesirable side-effects.

The pure estrogen phase at the beginning of the inventive treatment enables adequate proliferation of the endometrium. Reliable contraceptive protection is particularly achieved when, as described herein, the gestagen in the following combination phase is administered in twice the ovulation-inhibiting dose in the individual daily units. After ingesting the last of the gestagen-containing tablets, withdrawal bleeding occurs within a few days during the next estrogen phase, whereby a renewed proliferation of the endometrium is simultaneously stimulated due to the ingestion of the estrogen. In view of the previously described health risks, it is the embodiment of the invention where only natural estrogen is employed that is of great advantage, since especially low side-effects are anticipated in addition to adequate contraceptive reliability and cycle control.

The ovulation-inhibiting preparation of the present invention is utilized such that a defined number of daily hormone units such as dragees, tablets or the like of the first hormone constituent are orally administered on successive days for hormonal contraception within the desired cycle. The first hormone constituent consists essentially of an estrogen preparation as the hormonal agent. And that following thereupon, a defined plurality of daily hormone units such as dragees, tablets or the like of the second hormone constituent that consists of an estrogen preparation and a gestagen preparation in a dose at least adequate to inhibit ovulation in combination are orally administered. The first of the daily units of the first hormone constituent of the following cycle is administered the day following the administration of the last of the daily units of the second hormone constituent of the current cycle, so that a daily hormone unit is ingested every day, thereby eliminating administration pauses.

The bleeding which occurs with the ovulation-inhibiting preparation of the invention involves less blood loss and less pain as compared to preparations described in the prior art. This is due to the continuing estrogen administration. The contraceptive reliability of the present invention is also noticeably higher, because there are no administration-free days, not even a single day on which the contraceptive reliability could otherwise be overcome as a result of natural hormonal processes. Moreover, due to the lasting estrogen administration, a definite and positive, vessel-expanding effect occurs, thereby avoiding circulatory problems. A further advantage of the ovulation-inhibiting preparation of the invention is the suppression of the pre-menstrual syndrome with the use thereof. The syndrome can occur in the course of a natural cycle when estrogen is discontinued for only one day or for even a few days.

The uniform estrogen level that is achieved with use of the ovulation-inhibiting preparation of the invention also avoids the decrease of coagulation parameters during the hormone-free days and the following rise after the restoration of administration in the next cycle. The coagulation system in a stable equilibrium would otherwise be disturbed. The ovulation inhibiting preparation is, therefore, also particularly suitable for women over the age of 40. As is known, the risk of circulatory problems increases in this age group with increasing age.

The present invention further contemplates a method for hormonal contraception, comprising the step of administering the ovulation-inhibiting preparation described herein. In other words, a contraceptively active estrogen dose is thereby administered interruption-free, with gestagen doses being cyclically superimposed thereon.

By way of example and not limitation, the following examples of ovulation-inhibiting preparations serve to further illustrate principles of the present invention and its preferred embodiments.

EXAMPLE 1

A sequential preparation containing 7 daily units each having 4 mg estradiol as well as 21 daily units each having respectively 4 mg estradiol and 1 mg norethindrone acetate was used for ovulation-inhibiting treatment. The preparation was administered for a period of one year, resulting in practically no side-effects and extremely good contraceptive reliability. Intermenses occurred far more rarely with this preparation as compared to traditional low-dosage preparations.

EXAMPLE 2

An ovulation-inhibiting preparation in the form of a sequential preparation comprising 7 daily units, each having 2 mg estradiol valerate and 21 daily units, each having respectively 4 mg estradiol valerate and 2 mg chlormadinone acetate was used for hormonal contraception. The effectiveness corresponded to that described in Example 1.

EXAMPLE 3

An ovulation-inhibiting preparation was used with contained 10 daily units each having 20 µg ethinyl estradiol and 18 daily units each having respectively 20 µg ethinyl estradiol and 150 µg levonorgestrel. The results following administration of this preparation were similar to those of Example 1 and Example 2.

It should be understood that various changes and modifications to the presently preferred embodiments described herein will be apparent to those in the art. Such changes and modifications can be made without departing from the spirit and scope of the present invention and without diminishing its attendant advantages. It is, therefore, intended that such changes and modifications be covered by the appended claims.

We claim:

1. A method of hormonal contraception, comprising the step of:

administering to a woman an ovulation-inhibiting preparation comprising:

two hormone constituents packed spatially separate in a packing unit intended for chronological, sequential oral administration, said constituents each comprising a plurality of daily hormone units accommodated spatially separate and individually removable in the packing unit, wherein a first hormone constituent consists essentially of an estrogen preparation which effects a disturbance of the follicle stimulation, and a second hormone constituent consists of an estrogen preparation and gestagen preparation in a dosage at least adequate to inhibit ovulation;

the first daily hormone unit of the first hormone constituent of the following cycle is administered on the day following the administration of the last of the daily units of the second hormone constituent of the current cycle, whereby a daily hormone unit is ingested every day; and wherein the total number of daily hormone units is equal to the total number of days of the desired menstrual cycle of the woman and the number of daily units of the first hormone constituent is less than the number of daily units of the second hormone constituent, such that the first hormone constituent comprises five to fourteen daily units and the second hormone constituents comprises 23 to 14 daily units.

2. The method of claim 1, wherein at least one of the estrogen preparations is at least one hormone constituent from the group of hormones that quickly splits off ethinyl estradiol, mestranol, and other synthetic estrogens as well as at least one of the aforementioned hormone constituents after ingestion.

3. The method of claim 1, wherein at least one of the estrogen preparations is at least one hormone constituent from the group of hormones that quickly splits off estradiol, estrone, or other natural estrogens as well as at least one of the aforementioned hormone constituents after ingestion.

4. The method of claim 1, wherein the gestagen preparation is at least one hormone constituent from the group of hormones that quickly splits off progesterone, chlormadinone acetate, norethindrone acetate, cyproterone acetate, desogestrel, levonorgestrel, or other natural or synthetic gestagens as well as at least one of the aforementioned hormone constituents after ingestion.

5. The method of claim 1, wherein the total number of daily units is 28.

6. The method of claim 1, wherein the first hormone constituent comprises a maximum of 10 daily units.

7. The method of claim 1, wherein the number of daily units corresponds to the natural cycle of a woman.

8. In a method of hormonal contraception comprising the steps of:
administering to a woman an ovulation-inhibiting preparation comprising: two hormone constituents packed spatially separate in a packing unit intended for chronological, sequential oral administration, the constituents each comprising a plurality of daily hormone units accommodated spatially separate and individually removable in the packing unit, wherein a first hormone constituent consists essentially of an estrogen preparation which effects a disturbance of the follicle stimulation, and a second hormone constituent consists of an estrogen preparation and gestagen preparation in a dosage at least adequate to inhibit ovulation; wherein the number of daily units of the first hormone constituent being less than the number of daily units of the second hormone constituent, such that the first hormone constituent comprises 5 to 14 daily units and the second hormone constituent comprises 23 to 14 daily units; wherein the improvement comprises reducing or eliminating the incidence of estrogen-related side effects selected from the incidence of headache, hemostasis, circulatory problems, pre-menstrual syndrome and decrease of coagulation parameters by administering the first daily hormone unit of the first hormone constituent of the following cycle on the day following administration of the last of the daily units of the second hormone constituent of the current cycle, whereby a daily hormone unit is ingested every day and wherein the total number of daily hormone units is equal to the number of days of the desired menstrual cycle of the woman.

* * * * *